(12) United States Patent
Chell et al.

(10) Patent No.: US 7,006,594 B2
(45) Date of Patent: Feb. 28, 2006

(54) METHOD AND APPARATUS FOR RECONSTRUCTION CALIBRATION OF DETECTOR POSITION AND SOURCE MOTION BASED ON A MULTI-PIN PHANTOM

(75) Inventors: Erik Chell, Oakland, CA (US); John Couch, San Francisco, CA (US); Paul Magnuson, Hillsborough, CA (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 195 days.

(21) Appl. No.: 10/065,699

(22) Filed: Nov. 11, 2002

(65) Prior Publication Data

US 2003/0163271 A1 Aug. 28, 2003

Related U.S. Application Data

(60) Provisional application No. 60/359,562, filed on Feb. 25, 2002.

(51) Int. Cl.
*G01D 18/00* (2006.01)

(52) U.S. Cl. .......................................... 378/18; 378/207
(58) Field of Classification Search ................... 378/18, 378/207
See application file for complete search history.

(56) References Cited

U.S. PATENT DOCUMENTS

| | | | |
|---|---|---|---|
| 4,130,759 A | 12/1978 | Haimson | |
| 4,344,183 A | 8/1982 | Jacobson | |
| 4,613,754 A | * 9/1986 | Vinegar et al. | ........... 250/252.1 |
| 4,631,741 A | 12/1986 | Couch et al. | |
| 4,884,293 A | 11/1989 | Koyama | |
| 5,159,623 A | 10/1992 | Niepel | |
| 5,712,895 A | * 1/1998 | Negrelli et al. | .............. 378/207 |
| 5,761,268 A | 6/1998 | Voss et al. | |
| 5,923,727 A | 7/1999 | Navab | |
| 6,050,724 A | 4/2000 | Schmitz et al. | |

FOREIGN PATENT DOCUMENTS

| | | |
|---|---|---|
| DE | 19926098 A1 | 12/2000 |
| EP | 0874536 A1 | 10/1998 |

\* cited by examiner

*Primary Examiner*—Craig E. Church
(74) *Attorney, Agent, or Firm*—McAndrews, Held & Malloy, Ltd.; Peter J. Vogel; Michael A. Dellapenna

(57) ABSTRACT

Certain embodiments relate to a method and apparatus for calibrating an imaging system having an array of detector elements arranged with respect to a reference position and having an energy source moving in a pattern to irradiate the array of detector elements. The method includes initiating estimated detector positions for the array of detector elements and an estimated motion pattern for the energy source. The estimated detector positions and motion pattern are defined with respect to a reference position in the imaging system. The method further includes scanning a phantom having pins located at positions in the phantom and calculating estimated pin positions, with respect to the reference position, based on at least one of the estimated detector positions and motion pattern. The method further includes modifying at least one of the estimated detector positions and motion pattern based on at least two of the estimated detector positions, motion pattern and pin positions.

14 Claims, 5 Drawing Sheets

METHOD AND APPARATUS FOR RECONSTRUCTION CALIBRATION OF DETECTOR POSITION AND SOURCE MOTION BASED ON A MULTI-PIN PHANTOM

CROSS REFERENCE TO RELATED APPLICATIONS

The present application relates to, and claims priority from, co-pending application Ser. No. 10/065,700 filed on the same date as the present application and entitled "Method and Apparatus for Controlling Electron Beam Motion Based on Calibration Information". The present application relates to, and claims priority from, U.S. Provisional Application No. 60/359,562, filed on Feb. 25, 2002, and entitled "High-Precision Measurement of Projection Geometry for CT Using a Low-Precision Multipin Phantom". The provisional application names Erik Chell and John Couch as joint inventors, and the co-pending application names Erik Chell, John Couch, and Paul Magnuson as joint inventors. The co-pending and provisional applications are incorporated by reference herein in their entirety including the specifications, drawings, claims, abstracts and the like.

BACKGROUND OF INVENTION

The present invention generally relates to calibration of a medical diagnostic imaging system. In particular, the present invention relates to reconstruction calibration of detector position and source motion based on a multi-pin phantom.

Medical diagnostic imaging systems encompass a variety of imaging modalities, such as x-ray systems, computerized tomography (CT) systems, ultrasound systems, electron beam tomography (EBT) systems, magnetic resonance (MR) systems, and the like. Medical diagnostic imaging systems generate images of an object, such as a patient, for example, through exposure to an energy source, such as x-rays passing through a patient, for example. The generated images may be used for many purposes. For instance, internal defects in an object may be detected. Additionally, changes in internal structure or alignment may be determined. Fluid flow within an object may also be represented. Furthermore, the image may show the presence or absence of items in an object. The information gained from medical diagnostic imaging has applications in many fields, including medicine and manufacturing.

In order to help ensure that medical diagnostic images are reliable, it is advantageous to calibrate medical diagnostic imaging systems. The calibration of imaging systems is important for several reasons, including image quality and system performance. Poor image quality may prevent reliable analysis of an image. For example, a decrease in image contrast quality may yield an image that is not usable clinically. The calibration of medical imaging systems may help to produce a distinct and usable representation of an object.

The calibration of medical diagnostic systems is also important for safety reasons. For example, exposure to excessively high levels of x-ray energy may create certain health risk. Because of the health risk, governmental standards have been established for the use of x-ray systems. The level of x-ray energy emitted by an x-ray system may be measured in terms of radiation dosage. Calibration of x-ray systems and other medical diagnostic imaging systems may ensure that the radiation dosage to which the target is exposed does not exceed clinical standards.

One device that may be used in the calibration of medical diagnostic imaging system parameters, such as image quality and radiation dosage, is called a phantom. Many types of phantoms have been proposed. For example, phantoms may be physical replicas of imaging targets, such as human body parts. Another example of a phantom type is a physics-based phantom. A physics-based phantom may be comprised of various structures affixed to a common base. The structures of a physics-based phantom may possess varying characteristics, such as shape, size, density, composition, and arrangement, for example. Furthermore, physics-based phantoms may be constructed from various materials, including metal and plastic.

The structures of physics-based phantoms may affect characteristics of energy sources, such as x-rays, for example, which pass through the physics-based phantom. For example, metal structures may block x-rays. Additionally, plastic structures may merely decrease the energy level of received x-rays. A pattern resulting from the changes in the energy levels of received x-rays is represented in an x-ray image. The resulting pattern in the x-ray image may be easy to detect and analyze due to factors such as the contrast produced by the difference in received x-ray energy levels.

Phantoms may serve a variety of purposes. For example, phantoms may be used to practice positioning of an imaging target. Additionally, phantoms may be used to test parameters of the medical imaging system. Also, phantoms may be used to gauge the radiation dosage of energy emitted by the medical diagnostic imaging system. Furthermore, phantoms may be used for calibration and image quality assessment. However, for accurate positioning and system calibration, conventional phantoms are expensive and require high precision during manufacture. Thus, there is a need for a phantom that may accurately and easily determine component positions in a medical diagnostic imaging system. There is a need for an inexpensive phantom that may be used to calibrate a medical diagnostic imaging system which does not require high precision during manufacture or use.

In CT imaging systems, for example, an object such as a patient or a phantom is illuminated with x-rays from a plurality of angles to produce a set of x-ray projections. Each of the plurality of detectors in the imaging system samples the x-ray signal a plurality of times, and when the aggregate data from each detector is assembled with sample number on one axis and detector number on the other, the result is referred to as a sinogram. For example, if there are 1728 detectors in a CT system and each detector is sampled 864 times, the sinogram would be a matrix of 864×1728 x-ray attenuation values. The term "sinogram" derives from the sinusoidal shadow a solid object like a pin presents. The CT imaging system calculates or "reconstructs" a two dimensional image data from the sinogram data.

Inaccuracies in the CT imaging system may result in blurring, streaking, or introduction of ghost images or artifacts in the resulting image. For example, if a detector position or the center of a medical imaging system is inaccurate, an x-ray will be projected at an incorrect angle and produce an error in the resulting image. Thus, a need exists for a method and apparatus for more accurate calibration of a medical diagnostic imaging system.

Current calibration methods often involve time intensive or complicated procedures. Frequent calibration is required to help ensure consistent image quality. Additionally, existing calibration methods rely on the assumption that system components, such as detectors, have been accurately positioned and located. That is, conventional systems rely on the manufacturer's stated position of detectors and energy beam source in relation to the center of the imaging system. Accuracy may be time consuming and difficult to achieve, and error in the manufacturer's positioning may result in streaks on the images. Furthermore, current calibration methods require precise positioning of the phantom in order to properly calibrate the imaging system. Thus, a need exists for a method and apparatus for quick and easy system calibration. A need further exists for imaging system calibration using a low-precision phantom.

Additionally, EBT systems utilize a high energy beam of electrons to strike a target and produce x-rays for irradiating an object to be imaged. The point where the electrons strike the target is called the "beam spot". Dipole, quadrupole, and focusing coils may be used to deflect the electrons along the target to produce x-rays. Motion of the electron beam must be "tuned" to optimize beam motion and more accurately produce a beam spot.

Current methods of tuning EBT scanners involve sweeping the electron beam over "w" shaped wires ("W-wires") and evaluating the beam spot shape and position as a function of time. W-wires are expensive, however. Thus, there is a need for an inexpensive method of "tuning" or calibrating an electron beam. Additionally, in current EBT systems, only a small number of W-wires may fit (for example, 15 wires in current scanners), reducing accuracy of a tuning correction. Thus, there is a need for a system for more accurately tuning electron beam motion. Furthermore, in current systems, the W-wires are separated from the scanning targets. Therefore, a theoretical transfer function is currently necessary to move the beam from the W-wire target to the scanning target. Thus, a need exists for a method of measuring tune accurately on the scanning target itself, rather than on W-wires. There is a need for direct measurement and modification of electron beam currents based on actual imaging x-rays.

SUMMARY OF INVENTION

Certain embodiments of the present invention relate to a method and apparatus for calibrating an imaging system. Certain embodiments relate to a method for calibrating an imaging system having an array of detector elements arranged with respect to a reference position and having an energy source moving in a pattern to irradiate the array of detector elements. Calibration may result in more accurate measurement of detector positions and the motion of an electron beam spot as a function of time, which provides improved image quality to the imaging system. The method includes initiating estimated detector positions for the array of detector elements and an estimated motion pattern for the energy source. The estimated detector positions and motion pattern are defined with respect to a reference position in the imaging system. The method further includes scanning a phantom including pins and calculating estimated pin positions for the pins in the phantom, with respect to the reference position, based on at least one of the estimated detector positions and motion pattern. The method further includes modifying at least one of the estimated detector positions and motion pattern based on at least two of the estimated detector positions, motion pattern and pin positions.

Certain embodiments relate to a system for improved calibration of a diagnostic imaging system. The system includes an array of detector elements arranged with respect to a reference position, an energy source moving in a pattern to irradiate the array of detector elements, a phantom including pins and a reconstruction system calculating estimated pin positions for the pins in the phantom, with respect to the reference position, based on at least one of estimated detector positions and estimated motion pattern of the energy source. The reconstruction system modifies at least one of the estimated detector positions and motion pattern based on at least two of the estimated detector positions, motion pattern, and pin positions. In certain embodiments, the reconstruction system modifies at least one of the estimated detector positions and motion pattern by computing an error vector $\vec{E} = \vec{h} * \vec{P}$, wherein E represents an error associated with the estimated detector positions, motion pattern and/or pin positions (the geometrical parameters), h denotes adjustments to produce more accurate estimated detector positions, motion pattern and pin positions and P represents a matrix of derivatives for detector-phantom pin samples with respect to the detector positions, motion pattern and pin positions. The error vector E represents an error between empirical data in a sinogram and theoretical values obtained by evaluating the geometrical parameters in a model of the system. Solving for the h vector and using its values to modify detector positions, pin positions, and the beam spot motion pattern may result in improved knowledge of the actual geometry of the imaging system.

Certain embodiments relate to a multipin phantom for calibrating an imaging system. The phantom includes a block for housing a plurality of pins and a plurality of pins placed in the block to enable triangulation of detector elements of an imaging system.

Figure 1:
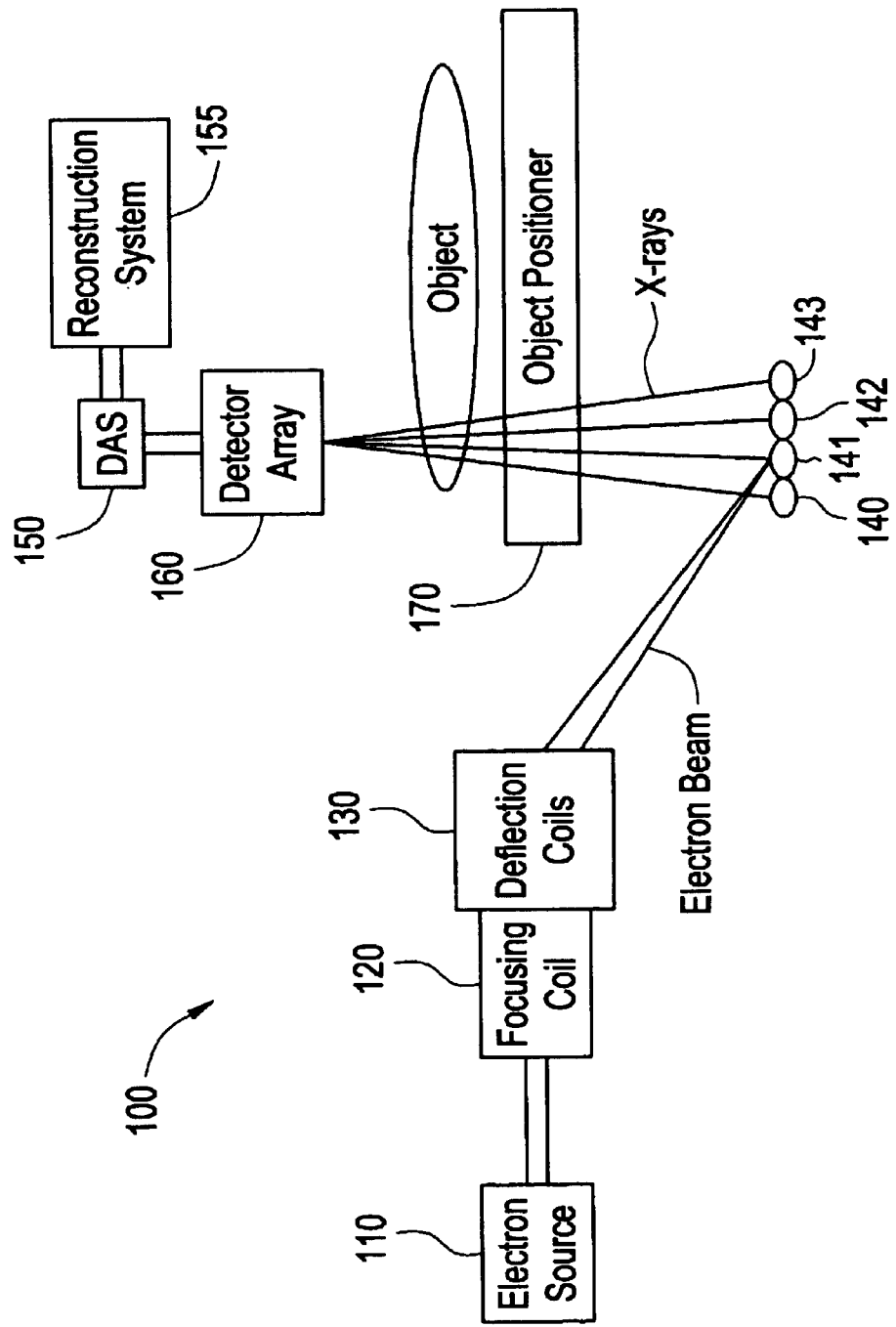
FIG. 1 illustrates an EBT imaging system used in accordance with an embodiment of the present invention.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentality shown in the attached drawings.

DETAILED DESCRIPTION

For the purpose of illustration only, the following detailed description references a certain embodiment of an Electron Beam Tomography (EBT) imaging system. It is understood that the present invention may be used with other imaging systems (such as computed tomography systems, and other imaging systems, for example).

FIG. 1 illustrates an EBT imaging system 100 formed in accordance with an embodiment of the present invention. The system 100 includes an electron source 110, a focusing coil 120, deflection coils 130, target rings 140–143, a data acquisition system (DAS) 150, a reconstruction system 155, a detector array 160, and an object positioner 170. As will be described further below, the electron source 110 generates an electron beam that travels to the focusing coil 120. At the focusing coil 120, the electron beam is focused to create a narrow, elliptical beam spot on the target rings 140–143. At the deflection coils 130, the electron beam is deflected to sweep along one of the target rings 140–143.

When the focused electron beam hits one of the target rings 140–143, the contacted target rings 140–143 emit a fan beam of x-rays. The point at which electrons from the electron beam are deflected onto the target ring 140 is referred to as the "beam spot" and serves as a source of imaging x-rays. In certain embodiments, there may be a single target ring 140 or a plurality of target rings 140–143, for example. In certain embodiments, the target rings 140–143 are made of tungsten. The electron beam may be swept along a 210 degree arc to produce, at each spot along the arc, a fan beam of x-rays.

The x-rays emitted from the target rings 140–143 pass through the object, such as a patient, for example, that is located on the object positioner 170. The object positioner 170 may be a table, a support, a wall bucky, or other movable or non-movable positioner, for example. The x-rays then impinge upon the detector array 160. The detector array 160 includes at least one row of detector elements. The detector elements of the detector array 160 generate signals in response to the impinging x-rays. The signals are transmitted from the detector array 160 to the DAS 150. The DAS 150 collects the data and sends the data to a reconstruction system 155. The reconstruction system 155 analyzes the signals and generates a medical diagnostic image from the data obtained from the detector array 160. The reconstruction system 155 may also store data or transmit data to an external processor or memory, for example. The reconstruction system 155 may be embodied in software and/or in hardware, for example.

The detector array 160 receives x-rays from several angles, along the arc over which the beam is swept, to produce a set of x-ray projections. The projection data is received by the DAS 150, and the total data from one sweep are arranged in a matrix called a sinogram. Within the sinogram, each row contains all projection data for one detector element, and each column contains data at a certain sample number for that detector element. From the two-dimensional sinogram of projection data, the reconstruction system 155 may reconstruct a two-dimensional image, typically characterizing an axial slice of the object imaged. Backprojection or another reconstruction technique may be used to reconstruct the two-dimensional image. The resulting image, however, may contain streaks or image artifacts (such as ghost images, for example) due to imperfections or inaccuracies in the system 100 and position of system 100 components. Examples of inaccuracies include errors in detector position or mischaracterization of the motion of the beam spot. Calibration of the system 100 may help to reduce or eliminate streaks or image artifacts to improve image quality. A phantom may be used to calibrate the system 100 to improve image quality and accuracy, for example.

Figure 2:
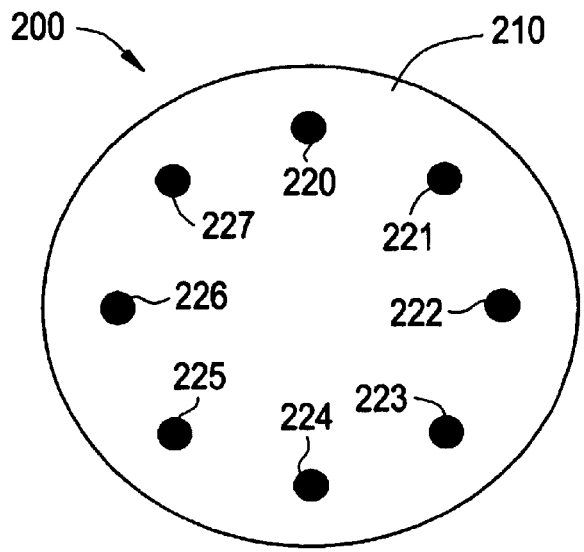
FIG. 2 illustrates a multipin phantom formed in accordance with an embodiment of the present invention.

FIG. 2 illustrates a multipin phantom 200 used for system geometrical calibration in accordance with an embodiment of the present invention. The multipin phantom 200 includes a block 210 of foam or other similar material. The multipin phantom 200 also includes a plurality of pins placed on or in the block 210. Multiple pins enable the phantom 200 to triangulate on system 100 components, such as the detector array 160 and the individual detectors of the detector array 160 and electron beam, for example, and obtain additional measurements, such as radius, motion, and position, for example. In certain embodiments, the multipin phantom 200 includes pins 220–227. The pins may include a metal, such as tungsten, for example. The pins 220–227 are placed roughly in a circle and are aligned along an axis of the detector array 160. The pins 220–227 may be enclosed in a cylinder of plastic for protection. The multipin phantom 200 may be attached to a smaller cylinder that allows the multipin phantom 200 to be mounted on a centermount of the object positioner 170.

Figure 3:
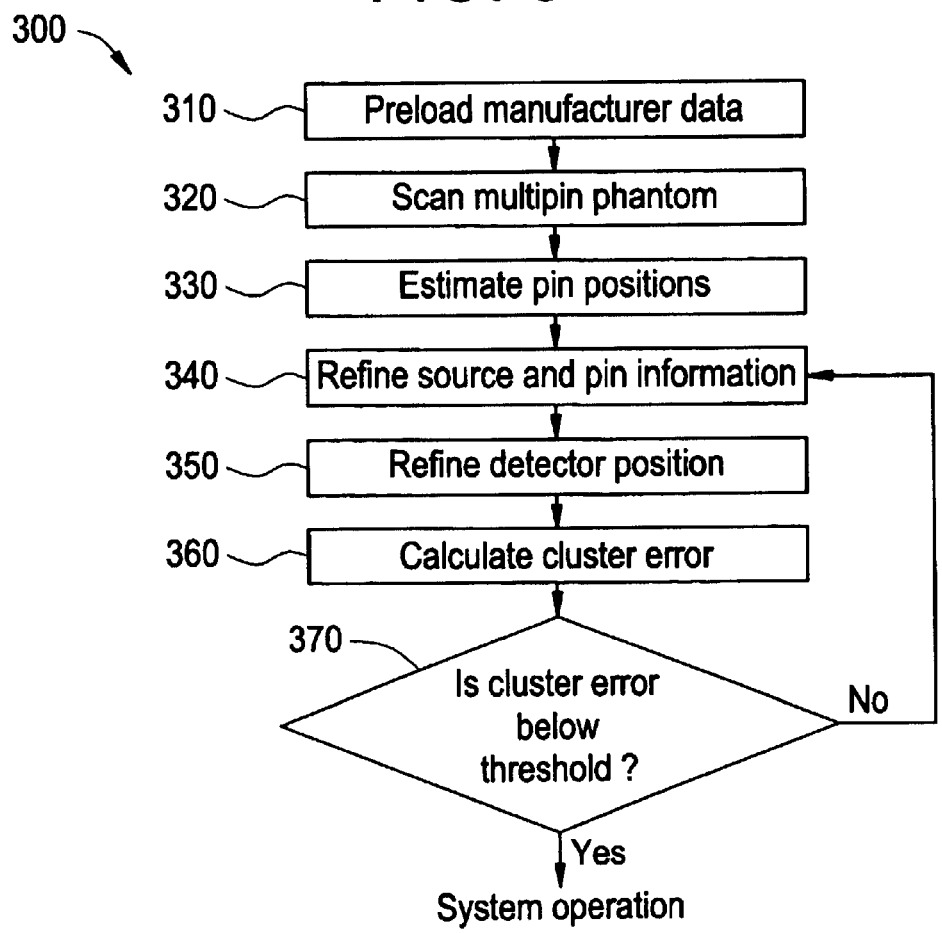
FIG. 3 illustrates a flow diagram for a method for calibrating a medical diagnostic imaging system in accordance with an embodiment of the present invention.

FIG. 3 illustrates a flow diagram 300 for a method for calibrating a medical diagnostic imaging system 100 in accordance with an embodiment of the present invention. After a brief overview, the steps of the method will be described in further detail below. First, at step 310, positions of the elements of the detector array 160, coefficients of energy beam or source motion, and other manufacturer information are preloaded. Then, at step 320, the multipin phantom 200 is placed on the object positioner 170, and a scan is acquired. Next, at step 330, phantom pin locations are analyzed. Using the theoretical locations of the elements in the detector array 160 and theoretical motion of the beam spot along the target rings 140–143, a rough estimation of the locations of pins 220–227 in the phantom 200 is made. Then, at step 340, the positions of the pins 220–227 and the motion of the beam spot along the target rings 140–143 is refined in a calculation that assumes the detector elements to be in their ideal location. At step 350, the refined pin positions and beam spot motion are used to refine the positions of the detector elements. At step 360, a quality metric called "cluster error" (defined below) is calculated and used to decide if the measurement of the detector element and beam spot positions is sufficient. If measurement is not sufficient, refinement continues in iterations of the above process.

Now the method of calibration will be described in more detail. First, at step 310, theoretical (or ideal or desired) component position data is preloaded. The theoretical data may be the expected position of the center of the detector array 160 and of the individual detector elements in the detector array 160, as well as coefficients describing the radial and angular motion of the beam spot produced by the energy source 110. The preload of desired data may be preceded by a blank scan to account for background or noise in the EBT imaging system 100. Then, at step 320, the multipin phantom 200 is scanned. The multipin phantom 200 may be placed on the object positioner 170, without concern for the precise location of the multipin phantom 200.

Next, at step 330, the positions of the detectors in the detector array 160 and the motion of the electron beam are "frozen" at the assumed or theoretical values. A scan with the multipin phantom 200 is performed. A sinogram is produced from irradiation of the multipin phantom 200 by radiation, such as x-rays, for example, from the target rings 140–143. By way of example only, 864 detector elements with 864 samples each may be included in the detector array 160, and eight pins 220–227 may be included in the multipin phantom 200. In this example, the sinogram obtained from the detector array 160 is an 864-by-864 sinogram.

Next, a trace of pins 220–227 through the sinogram is performed to identify the positions of individual pins 220–227 in the sinogram. Areas of high attenuation are assumed to be pin 220–227 shadows and are characterized for their central points and traced through the sinogram. Pin 220–227 position overlaps and other data may also be removed. By way of example, a sample may be obtained every 40 microseconds. The time at which the center of a pin 220–227 is detected may be a fractional sample number, such as sample number 1.25. With 864 detector elements and 8 pins, the result is an 864-by-8 table of pin 220–227 samples sorted by pin number (hereinafter, pin sample table). Pins 220–227 are identified by a sample number that corresponds to the time at which the sample was obtained (e.g., the time at which the center of the pin 220–227 was observed).

Then, at step 340, the detector array 160 position is "frozen" or held constant at the values calculated in step 330. New values for the coefficients describing the motion of the beam spot on the target rings 140–143 and pin 220–227 positions are refined from values obtained in previous steps. The mathematical method of this refinement will be described in detail below.

Next, at step 350, the source 110 and pin 220–227 positions are "frozen" or held constant at the values calculated in step 340, and the detector array 160 positions are refined. Detector position refinement proceeds in a manner similar to the pin 220–227 position refinement of step 340. In effect, pin 220–227 positions and electron beam or source 110 motion may be used to triangulate on each detector position in the detector array 160.

Then, at step 360, an assessment of the self-consistency of the set of equations describing the system 100 is made. Each entry in the pin sample table can be turned into a hypothetical ray from the detector element to the target ring 140–143. One end of the detector-target ray is defined by the position of the detector element, while the other is defined by the location of the beam spot at the time that detector element saw the pin 220–227.

Figure 4:
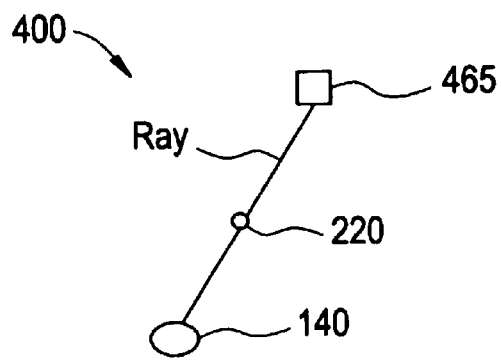
FIG. 4 illustrates ray tracing used in accordance with an embodiment of the present invention.

FIG. 4 illustrates a ray tracing 400 used in accordance with an embodiment of the present invention. In the ray tracing 400, a ray extends from a detector element 465 to the target ring 140. The actual position of the pin 220 may be unknown.

After all detector-target rays for a given pin 220–227 are determined, the "centroid" of the rays is computed. The centroid is defined as a position in space which minimizes, in a least squares sense, the distance of closest approach of each ray to the centroid. The centroid is then assumed to be the position of the pin 220–227 for subsequent calculations.

The least squares method is used to solve a set of equations with more equations than unknown variables. Accordingly, the answer achieved is not an exact solution but rather a solution that minimizes the sum of the squares of the residual errors.

Figure 5:
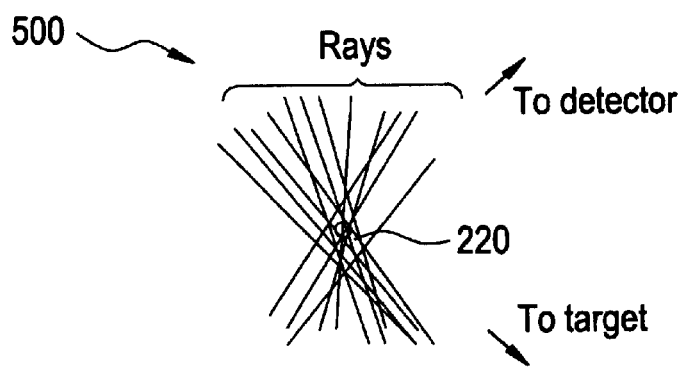
FIG. 5 illustrates a clustering of rays analyzed with a least-squares method used in accordance with an embodiment of the present invention.

FIG. 5 illustrates a clustering 500 of rays analyzed with a least-squares method used in accordance with an embodiment of the present invention. In FIG. 5, a plurality of rays from detector elements to the target ring 140–143 overlap to form the centroid in the region of the actual pin. The variation among the rays may be used to determine the accuracy of the system of equations describing the pin positions, detector element positions, and beam motion.

Once the centroid has been determined for all pins, a "cluster error" can be calculated. It is defined as the average distance by which each detector-target ray misses its own centroid. In a perfect system, cluster error would be zero. In practice, a cluster error of 5 microns, for example, usually indicates a sufficiently self-consistent solution for streak-free images.

At step 370, if the cluster error is above a certain threshold, refinement continues for the positions of the detector elements and the pins 220–227, along with source 110 motion as a function of time. Refinement continues according to the steps described above, starting at step 340, for example. For example, if the average distance by which rays miss the centroids of the pins 220–227 is more than ten microns, the refinement iterations continue. Each iteration of refinement may more precisely determine positions and characteristics. If the cluster error is below a certain threshold (ten microns, for example), the pin 220–227, detector array 160, and source 110 calculations are sufficient, and system 100 operation (e.g., imaging) may proceed. That is, the detector position and source 110 motion may be used in reconstruction of a medical diagnostic image through back-projection or other imaging method, for example.

While the answers obtained in the above calibration may not be perfect, the process may be iterated so that the solutions converge. In certain embodiments, calibration iterations converge to an answer in which an average ray will miss the centroid of its pin by no more than about three microns. An image generated after such calibration is virtually free of geometrically-caused streaks. Iterative calibration also provides an accurate description in radius and angle of beam spot motion along the target rings 140–143.

Figure 6:
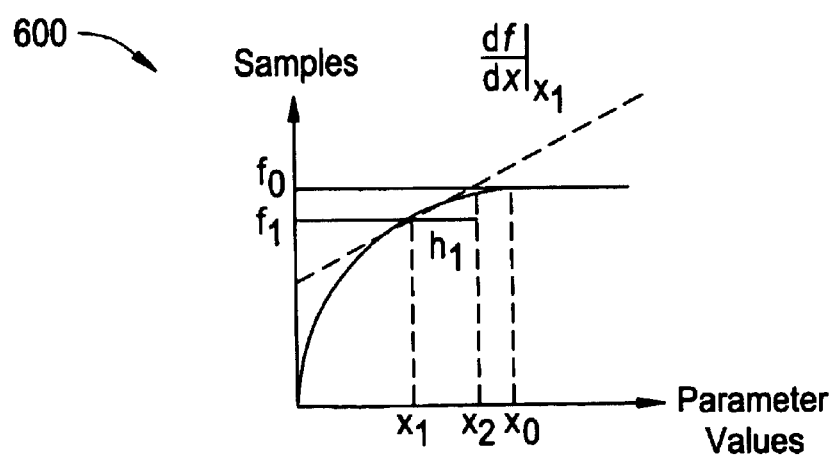
FIG. 6 shows a relationship, in a one dimensional case, between theoretical parameter values, actual parameter values, and the amount by which each parameter is to be changed used in accordance with an embodiment of the present invention.

The following is a discussion of the mathematical method used to refine system 100 parameters and component configuration. For example, first consider a one dimensional case represented in FIG. 6. Assume there is a variable parameter "x" and a theoretical function "f" that operates on parameter x. For an observed empirical value, $f(x_0)$, a value $x_0$ may be determined that will cause the function f to produce an observed empirical value $f(x_0)$. Analysis begins with an initial guess $x_1$ which, when acted upon by the theoretical function, produces a value $f(x_1)$. If the derivatives of function "f" may be calculated, a Taylor's series expansion is performed about point $x_1$, $$f(x_0) = f(x_1) + h \cdot \frac{df}{dx}\bigg|_{x_1} + \frac{1}{2}h^2 \cdot \frac{d^2 f}{d^2 x}\bigg|_{x_1} + \dots \quad (1)$$

Since $f(x_0)$ is a known, empirical value, solving for "h" may reveal how much to vary $x_1$ to produce $x_0$, the unknown quantity. Solving for h is impractical, however, so the series is simplified to ignore second-order and higher terms. The resulting equation is $$f(x_0) \cong f(x_2) = h_1 \cdot \frac{df}{dx}\bigg|_{x_1}. \quad (2)$$

Equation 2 may be solved for $h_1$, giving an approximate solution for an improved "x", $$x_2 = x_1 + h_1 \quad (3).$$

Proceeding in this fashion, approximations may be refined to produce $x_3$, $x_4$, etc., each of which is closer to the desired value $x_0$. That is, the input parameter may be refined until the theoretical function acting on the input parameter produces the desired observed value.

However, rather than simply solving for a one-dimensional "x", multiple parameters may be simultaneously optimized to produce a close theoretical match to thousands of detector-pin "events" visible in the sinogram of the multipin phantom 200. The parameters include positions of each pin 220–227, positions of the detector elements in the detector array 160, and the coefficients of the Fourier series describing the motion of the electron beam source in radius and angle, for example. Therefore, for a given detector element d and a given pin p, the error (difference between theoretical sample prediction $q_s$ and measured sample number $q_m$) may be written as $$q_m^{d,p} - q_s^{d,p} \approx \frac{\partial q^{d,p}}{\partial R_p}\bigg|_s \cdot \nabla R_p + \frac{\partial q^{d,p}}{\partial \theta_p}\bigg|_s \cdot \nabla \theta_p + \sum_j^{ncoefs} \frac{\partial q^{d,p}}{\partial rc_j}\bigg|_s \cdot \nabla rc_j + \sum_j^{ncoefs} \frac{\partial q^{d,p}}{\partial ac_j}\bigg|_s \cdot \nabla ac_j, \quad (4)$$

where $R_p$ represents the radius of pin P, $\theta_p$ represents the angle of pin P, $rc_j$ represents the $j^{th}$ radial coefficient of beam motion, and $ac_j$ represents the $j^{th}$ angular coefficient of beam motion.

In other words, the measured sample value of pin p in detector element d is roughly equal to the theoretical value plus the derivative of the sample function with respect to pin p's radius times $\nabla R$, plus the derivative with respect to pin p's angle times $\nabla \theta$, plus the derivatives multiplied by the deltas of the source coefficient terms, etc. A desired result of the calculation is the values of the deltas ("▽") that minimize the difference between measured pin sample values and theoretical values obtained by applying the system model ("f") to the parameter values (i.e., pin position, beam motion coefficients, etc.).

While equation (4) is one equation with multiple unknowns, creating simultaneous equations for all pins 220–227 seen by all detector elements in the detector array 160 results in more equations than unknowns. By casting the problem into a system of linear equations, an adjustment to the parameters (represented by the vector h) may be determined using singular value decomposition (SVD). SVD minimizes, in a least-squares sense, the disagreement between theoretical sample values and the empirically measured values. Thus, equation (4) may be generalized to a system of equations denoted by $$\vec{E} = \vec{h} \cdot P \qquad (5),$$

where $\vec{E}$ represents the error or the difference between measurement and theory of each detector-pin combination, the vector $\vec{h}$ denotes adjustments or deltas for individual parameters to produce more accurate theoretical sample values, and P represents the matrix of partial derivatives of each detector-pin sample with respect to individual parameters.

The error vector $\vec{E}$ may be represented as follows: detector 1 detector 2 ... detector n $$\vec{E} = [e_1^1, e_2^1, e_3^1, \ldots, e_{npins}^1, e_2^2, e_3^2, \ldots, e_{npins}^2, \ldots, e_1^n, e_2^n, e_3^n, \ldots, e_{npins}^n], \qquad (6)$$

where $$e_p^d$$

denotes a difference between empirical data and theory in the sample number of pin p as seen by detector d. The vector of parameter changes may be represented as follows:

$$\vec{h} = [\Delta R_{p1}, \Delta\theta_{p1}, \Delta R_{p2}, \Delta\theta_{p2}, \ldots, \Delta rc_1, \Delta rc_2, \Delta rc_3, \ldots, \Delta ac_1, \Delta ac_2, \Delta ac_3, \ldots] \qquad (7)$$

where $\Delta R_p$ denotes a change in radius of pin p, $\Delta\theta_p$ represents a change in angle of pin p, $\Delta_{rc}$ represents a change in radial source coefficient, and $\Delta_{ac}$ denotes a change in angular source coefficient. The matrix of derivatives P is shown below. In practice, pin position cross terms may be set to zero, as a deviation in the position of one pin position has only a second order effect on another pin position.

$$P = \begin{bmatrix} \frac{\partial q^{11}}{\partial R_{p1}} & \frac{\partial q^{11}}{\partial \theta_{p1}} & \frac{\partial q^{11}}{\partial R_{p2}} & \frac{\partial q^{11}}{\partial \theta_{p2}} & \cdots & \frac{\partial q^{11}}{\partial rc_1} & \frac{\partial q^{11}}{\partial rc_2} & \cdots & \frac{\partial q^{11}}{\partial ac_1} & \frac{\partial q^{11}}{\partial ac_2} & \cdots \\ \frac{\partial q^{12}}{\partial R_{p1}} & \frac{\partial q^{12}}{\partial \theta_{p1}} & \frac{\partial q^{12}}{\partial R_{p2}} & \frac{\partial q^{12}}{\partial \theta_{p2}} & \cdots & \frac{\partial q^{12}}{\partial rc_1} & \frac{\partial q^{12}}{\partial rc_2} & \cdots & \frac{\partial q^{12}}{\partial ac_1} & \frac{\partial q^{12}}{\partial ac_2} & \cdots \\ \frac{\partial q^{13}}{\partial R_{p1}} & \frac{\partial q^{13}}{\partial \theta_{p1}} & \frac{\partial q^{13}}{\partial R_{p2}} & \frac{\partial q^{13}}{\partial \theta_{p2}} & \cdots & \frac{\partial q^{13}}{\partial rc_1} & \frac{\partial q^{13}}{\partial rc_2} & \cdots & \frac{\partial q^{13}}{\partial ac_1} & \frac{\partial q^{13}}{\partial ac_2} & \cdots \\ & & & & \cdots & & & \cdots & & & \cdots \\ \frac{\partial q^{21}}{\partial R_{p1}} & \frac{\partial q^{21}}{\partial \theta_{p1}} & \frac{\partial q^{21}}{\partial R_{p2}} & \frac{\partial q^{21}}{\partial \theta_{p2}} & \cdots & \frac{\partial q^{21}}{\partial rc_1} & \frac{\partial q^{21}}{\partial rc_2} & \cdots & \frac{\partial q^{21}}{\partial ac_1} & \frac{\partial q^{21}}{\partial ac_2} & \cdots \\ \frac{\partial q^{22}}{\partial R_{p1}} & \frac{\partial q^{22}}{\partial \theta_{p1}} & \frac{\partial q^{22}}{\partial R_{p2}} & \frac{\partial q^{22}}{\partial \theta_{p2}} & \cdots & \frac{\partial q^{22}}{\partial rc_1} & \frac{\partial q^{22}}{\partial rc_2} & \cdots & \frac{\partial q^{22}}{\partial ac_1} & \frac{\partial q^{22}}{\partial ac_2} & \cdots \\ \frac{\partial q^{23}}{\partial R_{p1}} & \frac{\partial q^{23}}{\partial \theta_{p1}} & \frac{\partial q^{23}}{\partial R_{p2}} & \frac{\partial q^{23}}{\partial \theta_{p2}} & \cdots & \frac{\partial q^{23}}{\partial rc_1} & \frac{\partial q^{23}}{\partial rc_2} & \cdots & \frac{\partial q^{23}}{\partial ac_1} & \frac{\partial q^{23}}{\partial ac_2} & \cdots \\ & & & & \cdots & & & \cdots & & & \cdots \\ \frac{\partial q^{n1}}{\partial R_{p1}} & \frac{\partial q^{n1}}{\partial \theta_{p1}} & \frac{\partial q^{n1}}{\partial R_{p2}} & \frac{\partial q^{n1}}{\partial \theta_{p2}} & \cdots & \frac{\partial q^{n1}}{\partial rc_1} & \frac{\partial q^{n1}}{\partial rc_2} & \cdots & \frac{\partial q^{n1}}{\partial ac_1} & \frac{\partial q^{n1}}{\partial ac_2} & \cdots \\ \frac{\partial q^{n2}}{\partial R_{p1}} & \frac{\partial q^{n2}}{\partial \theta_{p1}} & \frac{\partial q^{n2}}{\partial R_{p2}} & \frac{\partial q^{n2}}{\partial \theta_{p2}} & \cdots & \frac{\partial q^{n2}}{\partial rc_1} & \frac{\partial q^{n2}}{\partial rc_2} & \cdots & \frac{\partial q^{n2}}{\partial ac_1} & \frac{\partial q^{n2}}{\partial ac_2} & \cdots \\ \frac{\partial q^{n3}}{\partial R_{p1}} & \frac{\partial q^{n3}}{\partial \theta_{p1}} & \frac{\partial q^{n3}}{\partial R_{p2}} & \frac{\partial q^{n3}}{\partial \theta_{p2}} & \cdots & \frac{\partial q^{n3}}{\partial rc_1} & \frac{\partial q^{n3}}{\partial rc_2} & \cdots & \frac{\partial q^{n3}}{\partial ac_1} & \frac{\partial q^{n3}}{\partial ac_2} & \cdots \\ & & & & \cdots & & & \cdots & & & \cdots \end{bmatrix} \begin{matrix} \text{pin 1} \\ \text{pin 2} \quad \text{detector 1} \\ \text{pin 3} \\ \\ \text{pin 1} \\ \text{pin 2} \quad \text{detector 2} \\ \text{pin 3} \\ \\ \text{pin 1} \\ \text{pin 2} \quad \text{detector } n \\ \text{pin 3} \\ \end{matrix} \qquad (8)$$

pin positions     rad. coeffs.     ang. coeffs.

The matrix P includes a number of rows equal to the number of detector elements n in the detector array 160 in the system 100 multiplied by the number n of pins 220–227. The number of columns in the matrix P is equal to twice the number n of pins 220–227 (one term for each radius, one term for each angle) plus the number of source coefficients. The first set of columns represents derivative terms for the pin positions, varying the radius and angle of each pin according to sample number. The second set of columns varies the radius coefficients of the source electron beam. The third set of columns varies the angle coefficients of the source.

Calculation of the derivative terms may be accomplished numerically. Once the equation E=h*P is set up, the solution involves using a singular value decomposition (SVD) algorithm to solve for h. Values in the vector h may be added to the initial parameters to provide a more accurate list of pin 220–227 positions and source 110 coefficients. Improved detector element positions may also be calculated. Solving for detector element positions by adding detector element positions to the system of equations results in too large of a solution space for current off-the-shelf computers. Thus, a separate "clustering" method may be used in which detector element positions are solved for individually. For each detector element, the source coefficients are evaluated at the times of each pin 220–227 sighting (yielding the source 110 positions). Rays may be drawn from the target 140–143 through the pins 220–227. A point of convergence is calculated. The detector element position is updated to the point of convergence, barring errors or unlikely results. The process of setting up the system of equations, solving the system, and clustering of detector elements may then be repeated until a sufficient answer is obtained.

In certain embodiments, motion and other characteristics of the energy beam may be modified based on the above described calibration method. For example, iterative calibration of the detector array 160 and energy source 110 is performed, as described above in reference to FIGS. 1, 2 and 3. Then, beam spot motion information is used to adjust currents applied to the deflection coils 130 coils. A complete set of coil currents for a scan is called a "tune".

Figure 7:
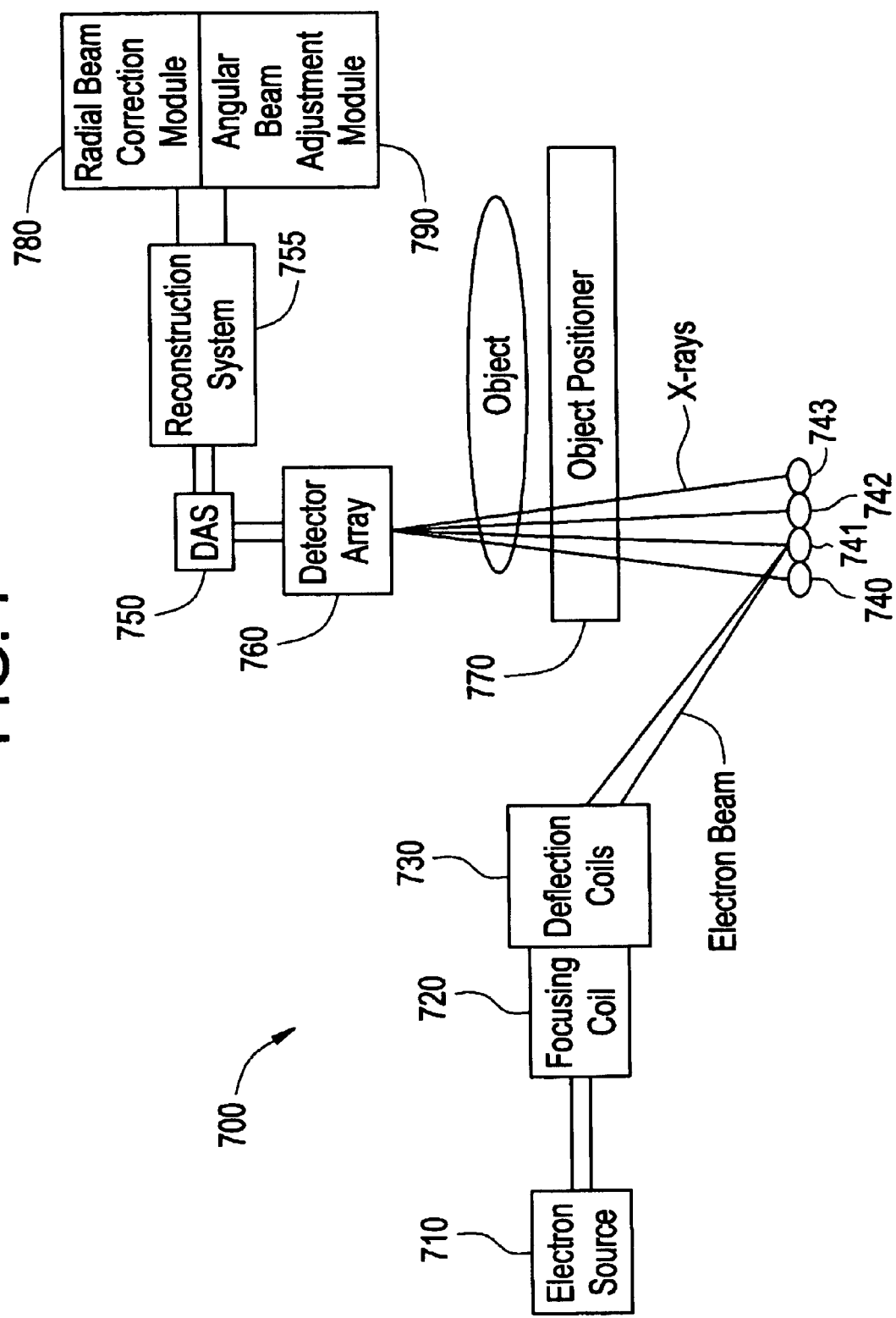
FIG. 7 illustrates an electron beam tuning system used in accordance with an embodiment of the present invention.

FIG. 7 illustrates an electron beam tuning system 700 formed in accordance with an embodiment of the present invention. The system 700 includes a radial beam correction module 780 and an angular beam adjustment module 790. The radial beam correction module 780 and the angular beam adjustment module 790 may be separate units or may be combined in a single unit. The radial beam correction module 780 and the angular beam adjustment module 790 may be embodied in hardware and/or in software. The system 700 may be used in conjunction with an electron source 710, a focusing coil 720, deflection coils 730, target rings 740–743, a DAS 750, a reconstruction system 755, a detector array 760, an object positioner 770, and a multipin phantom 775. The electron source 710, focusing coil 720, deflection coil 730, target rings 740–743, DAS 750, reconstruction system 755, detector array 760, object positioner 770, and multipin phantom 775 are similar to the components described above in relations to FIG. 1 and FIG. 2.

In operation, tuning is similar to calibration described above. The multipin phantom 775 is placed on the object positioner 770 without particular regard to accuracy. A scan is acquired. Then, the iterative computations previously described are performed to characterize the motion of the beam spot along the target rings 140–143.

Once beam spot and/or electron beam motion have been determined, coil currents may be adjusted to optimize beam spot and/or electron beam movement. Coil currents for the deflection coil are stored as a series of deflection update blocks (DUBs). A DUB represents a single "quantum" of coil currents sent to each deflection coil. In certain embodiments, a DUB is stored for every twenty microseconds. Thus, a single deflection buffer may contain thousands of DUBs.

In correcting radial fluctuations of the motion of the beam spot along the target rings 140–143, the radius of the beam spot is examined at the time of each DUB. If the radius is too large (too much deflection), the dipole currents in the deflection coil are decreased by a scale factor proportional to the size of the deviation from an ideal tune. If the radius is too small (not enough deflection), the dipole currents are increased by a scale factor proportional to the size of the deviation from an ideal tune. By going through each DUB and scaling the dipole currents, a tune that is substantially flatter and closer to an ideal tune than the original tune may be obtained. The above process may be iterated (rescan the multipin phantom 775 with the new tune, redo the multipin phantom 775 calibration, and re-correct the deflection buffers) to produce a set of coil currents with a desired radial flatness.

The angular motion of the electron beam may also be adjusted using information from the multipin phantom 775. An optimal tune produces a beam spot that moves with a constant angular velocity. An initial tune may have angular accelerations and decelerations. Deviations from the desired angular velocity may be flattened out on a DUB-by-DUB basis. Each DUB corresponds to a specified time; hence the desired angular position of the beam spot for each DUB is known. The actual angular position at a given time is contained in a beam spot position file calculated using the multipin phantom 775. Although the beam spot goes through all the correct angles, the beam spot may not be at the correct angle at the correct time.

By searching through the existing DUBs and beam spot position file, coil currents may be found that will place the electron beam at the desired position for any given DUB. These currents are then interpolated and loaded into the DUB that is being optimized. For example, assume that the DUB at 25 milliseconds is the one being optimized. It may be that the desired location of the beam spot at this time is the 6 o'clock position. However, the actual beam spot may be at the 6 o'clock position at a different time, for example t=24.985 ms. In that case, the coil currents in the two DUBS spanning 24.985 ms would be linearly interpolated and placed in the DUB at 25 ms. Linear interpolation or combination will help ensure that the beam spot will be at the 6 o'clock position at 25 ms into the scan.

Linear combination is performed for every DUB in the deflection buffer. Through linear combination, the angular deviations are "flattened," and a constant angular velocity is approached. In some embodiments, the flattening process is iterated to approach the desired angular velocity. Physical limitations of the deflection coil 730 and focusing coil 720 and effects of the previously described radial modifications being performed along with the angular modifications may result in iteration.

Figure 8:
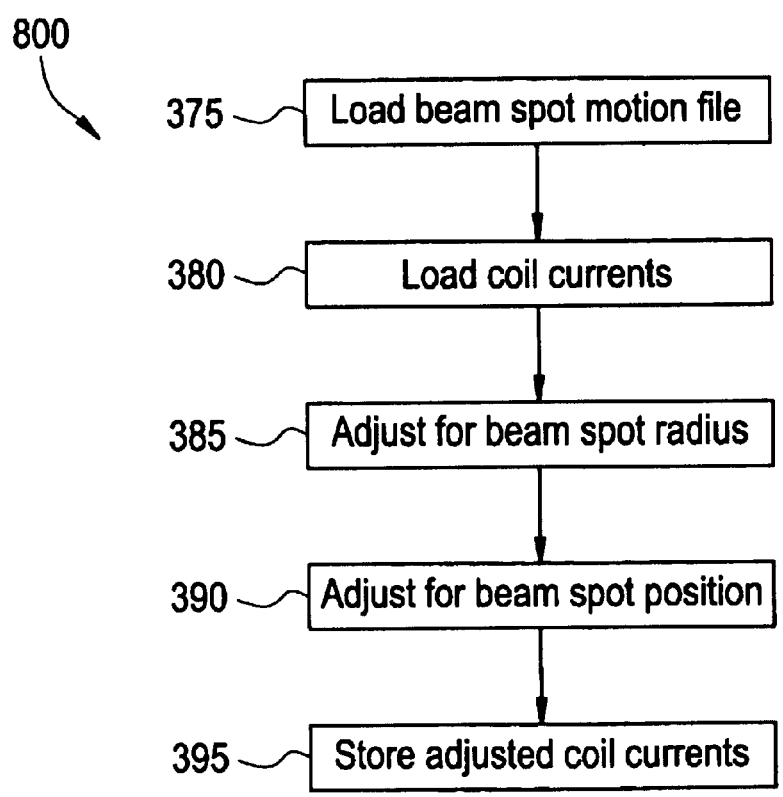
FIG. 8 illustrates a flow diagram for a method for adjusting an electron beam in accordance with an embodiment of the present invention.

FIG. 8 illustrates a flow diagram 800 for a method for adjusting an electron beam used in accordance with an embodiment of the present invention. First, pin positions, detector element positions, and electron beam motion parameters are determined through estimation and refinement according to steps 310–370 described above. When detector element positions and electron beam motion have been computed, the electron beam may be adjusted as described below.

Electron beam and beam spot motion parameters, as well as other parameters, such as pin positions and detector element positions, may be stored in a file. At step 375, the file, such as the beam spot motion file, may be loaded or retrieved in the system 700 for use in adjusting the electron beam.

At step 380, currents for the deflection coils 730 are loaded from a series of deflection update blocks (DUBs). Then, at step 385, the radius of the electron beam spot is examined at the time of each DUB. If the radius is too large (indicating too much deflection, for example), the dipole currents in the deflection coil are decreased by a scale factor proportional to the size of the deviation from an ideal coil current or tune. If the radius is too small (indicating not enough deflection, for example), the dipole currents are increased by a scale factor proportional to the size of the deviation from an ideal tune.

Next, at step 390, DUBS are adjusted to put the beam at a proper angle as a function of time. Using the search and interpolation method described above, the coil currents are modified to make the beam spot sweep along the targets 140–143 with the correct constant angular velocity.

Finally, at step 395, the adjusted coil current values are stored. The adjusted coil currents aim and focus the electron beam in the electromagnetic focusing coil 20 and deflection coils 730 to strike a desired position on the target rings 740–743 at a desired time. The above steps may be repeated as necessary to adjust the electron beam.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A method for calibrating an imagine system having an array of detector elements arranged with respect to a reference position and having an energy source moving in a pattern to irradiate the array of detector elements, the method comprising:

initiating estimated detector positions for the array of detector elements and an estimated motion pattern for the energy source, said estimated detector positions and motion pattern being defined with respect to a reference position in the imaging system;

scanning a phantom having pins located at positions in the phantom;

calculating estimated pin positions for the pins in the phantom, with respect to the reference position, based on at least one of said estimated detector positions and motion pattern; and modifying at least one of said estimated detector positions and motion pattern based on at least two of said estimated detector positions, motion pattern and pin positions.

2. The method of claim 1, further comprising determining an amount of error in at least one of said estimated detector positions, motion pattern and pin positions; and, when the amount of error exceeds a threshold, repeating said calculating and modifying steps.

3. The method of claim 1, further comprising:

repeating said calculating and modifying steps at least once to obtain first and second estimated detector positions, motion pattern and pin positions; and calculating an amount of error between said first and second estimated detector positions, motion pattern and pin positions.

4. The method of claim 1, further comprising:

drawing rays between associated points along said estimated motion pattern of the energy source and said estimated detector positions; and utilizing points of intersection between the rays to calculate said estimated pin positions.

5. The method of claim 1, further comprising:

determining actual pin positions from the scan of the phantom; and calculating a difference between said estimated and actual pin positions.

6. The method of claim 1, further comprising:

determining actual pin positions:

calculating a pin error representing an amount by which said estimated pin positions differed from said actual pin positions; and modifying said estimated detector positions based on the pin error.

7. The method of claim 1, further comprising:

determining actual pin positions;

calculating a pin error representing an amount by which said estimated pin positions differed from said actual pin positions; and modifying said estimated motion pattern for the energy source based on the pin error.

8. The method of claim 1, wherein said motion pattern of the energy source comprises an arc.

9. The method of claim 1, wherein said modifying step further comprises computing an error vector E=h*P, wherein E represents an error associated with at least one of said estimated detector positions, motion pattern and pin positions, h denotes adjustments to produce more accurate estimated detector positions, motion pattern and pin positions and P represents a matrix of derivatives for detector-phantom pin samples with respect to said detector positions, motion pattern and pin positions.

10. The method of claim 1, wherein the phantom is positioned in the imaging system independent of the reference position.

11. A system for improved calibration of a diagnostic imaging system, said system comprising:

an array of detector elements arranged with respect to a reference position;

an energy source moving in a pattern to irradiate said array of detector elements;

a phantom having pins located at positions in said phantom; and a reconstruction system calculating estimated pin positions for said pins in said phantom, with respect to said reference position, based on at least one of estimated detector positions and estimated motion pattern of said energy source, said reconstruction system modifying at least one of the estimated detector positions and motion pattern based on at least two of the estimated detector positions, motion pattern, and pin positions.

12. The system of claim 11, wherein said reconstruction system modifies at least one of the estimated detector positions and motion pattern by computing an error vector E=h*P, wherein E represents an error associated with at least one of the estimated detector positions, motion pattern and pin positions, h denotes adjustments to produce more accurate estimated detector positions, motion pattern and pin positions and P represents a matrix of derivatives for detector-phantom pin samples with respect to the detector positions, motion pattern and pin positions.

13. The system of claim 11, wherein the motion pattern of said energy source comprises an arc.

14. The system of claim 11, wherein said reconstruction system determines an amount of error in at least one of the estimated detector positions, motion pattern; and pin positions, and, when the amount of error exceeds a threshold, said reconstruction system repeats calculating and modifying at least one of estimated detector positions, motion pattern and pin positions.

* * * * *